US00PP22437P2

(12) United States Plant Patent
Smith

(10) Patent No.: US PP22,437 P2
(45) Date of Patent: Jan. 3, 2012

(54) ***CHRYSANTHEMUM* PLANT NAMED 'SYNBERNA YEL'**

(50) Latin Name: *Chrysanthemum×morifolium*
Varietal Denomination: Synberna Yel

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/925,043

(22) Filed: Oct. 12, 2010

(51) Int. Cl.
*A01H 5/00* (2006.01)

(52) U.S. Cl. ..... Plt./295

(58) Field of Classification Search ..... Plt./295
See application file for complete search history.

*Primary Examiner* — Annette Para
(74) *Attorney, Agent, or Firm* — S. Matthew Edwards

(57) ABSTRACT

A new *Chrysanthemum* plant named 'Synberna Yel' particularly distinguished by the large, long lasting flowers with yellow ray florets, rounded plant habit with yellow-green foliage, a garden *Chrysanthemum* with an early flowering natural season habit.

1 Drawing Sheet

Latin name of the genus and species of the plant claimed: *Chrysanthemum×morifolium.*

Varietal denomination: 'Synberna Yel'.

BACKGROUND OF THE NEW PLANT

The present invention comprises a new *Chrysanthemum,* botanically known as *Chrysanthemum×morifolium,* and hereinafter referred to by the variety name 'Synberna Yel'.

'Synberna Yel' is a product of a planned breeding program. The new cultivar has large, long lasting flowers with yellow ray florets, rounded plant habit with yellow-green foliage, a garden *Chrysanthemum* with a natural flowering season of about mid-September.

'Synberna Yel' originated from a hybridization made in October 2004 in a controlled breeding environment in Salinas, Calif. The female parent was the unpatented proprietary plant designated '01-M16' with white spooned shaped ray florets and a less vigorous plant habit.

The male parent of 'Synberna Yel' was the proprietary plant designated 'Yogwendolyn', U.S. Plant Pat. No. 17,533, with white ray florets and a one week faster natural season flowering response. The resultant seed was sown in June 2005 in Alva, Fla.

'Synberna Yel' was selected as one flowering plant within the progeny of the stated cross in the late October 2005 in a controlled environment in Alva, Fla.

The first act of asexual reproduction of 'Synberna Yel' was accomplished when vegetative cuttings were propagated from the initial selection in December 2005 in a controlled environment in Alva, Fla.

BRIEF SUMMARY OF INVENTION

Horticultural examination of plants grown from cuttings of the plant initiated in December 2005, and continuing thereafter, has demonstrated that the combination of characteristics as herein disclosed for 'Synberna Yel' are firmly fixed and are retained through successive generations of asexual reproduction.

'Synberna Yel' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6761). 'Synberna Yel' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Synberna Yel' with colors being as true as possible with an illustration of this type. The photographic drawing shows a flowering potted plant of the new variety, and a close-up of the flowers.

DETAILED BOTANICAL DESCRIPTION

The plant descriptions, measurements and aforementioned photographs were taken in Gilroy, Calif. in October 2009 under natural light. These plants were grown in an outdoor trial. These plants were about 12-14 weeks old.

Color references are made to The Royal Horticultural Society Colour Chart (R.H.S.) 2001.

TABLE I

DIFFERENCES BETWEEN THE NEW VARIETY 'SYNBERNA YEL' AND A SIMILAR VARIETY: 'YOANNA' (U.S. Plant Pat. No. 7,847)

| | 'Synberna Yel' | 'Yoanna' (U.S. Plant Pat. No. 7,847) |
|---|---|---|
| Flowering response: | Plants flower more uniformly | Less uniformly |
| Plant habit: | Much rounder | Less rounded |

TABLE I-continued

DIFFERENCES BETWEEN THE NEW VARIETY 'SYNBERNA YEL' AND A SIMILAR VARIETY: 'YOANNA' (U.S. Plant Pat. No. 7,847)

| | 'Synberna Yel' | 'Yoanna' (U.S. Plant Pat. No. 7,847) |
|---|---|---|
| Flower timing: | Natural season response is more consistent from north to south | Natural season response is less consistent from north to south |

Plant:
- *Form, growth and habit.*—Herbaceous decorative garden type; stems upright and outwardly spreading, freely branching, strong and moderately vigorous growth habit.
- *Plant height.*—22 cm.
- *Plant height (inflorescence included).*—32-34 cm.
- *Plant width.*—About 33-36 cm.
- *Garden performance and tolerance to weather.*—Very good.

Roots:
- *Number of days to initiate roots.*—4 days at about 22 degrees C.
- *Number of days to produce a rooted cutting.*—10-12 days at 22 degrees C.
- *Type.*—Fine, fibrous, free branching.
- *Color.*—RHS N155B but whiter.

Foliage:
- *Arrangement.*—Alternate, simple.
- *Immature, leaf color, upper surface.*—RHS 146A but more green.
- *Lower surface.*—RHS 147B.
- *Mature, leaf color, upper surface.*—RHS 146A but more green.
- *Lower surface.*—RHS 147B.
- *Length.*—5.0-5.5 cm.
- *Width.*—3.7-4.2 cm.
- *Shape.*—Ovate.
- *Base shape.*—Attenuate.
- *Apex shape.*—Mucronulate.
- *Margin.*—Palmately lobed, irregularly incised; serrate.
- *Texture, upper surface.*—Bifid T-shaped hairs.
- *Lower surface.*—Bifid T-shaped hairs.
- *Color of veins, upper surface.*—RHS 146C.
- *Color of veins, lower surface.*—RHS 146C.
- *Petiole color.*—RHS 146B.
- *Length.*—1.5-1.9 cm.
- *Diameter.*—0.2 cm.
- *Texture.*—Bifid T-shaped hairs.

Stem:
- *Quantity of main branches per plant.*—About 12.
- *Quantity of leaves per branch.*—About 12.
- *Color of stem.*—RHS 146B.
- *Length of stem.*—About 20 cm.
- *Diameter.*—0.4-0.5 cm.
- *Length of internodes.*—0.7-1.5 cm.
- *Texture.*—Bifid T-shaped hairs.
- *Color of peduncle.*—Closest to RHS 147B.
- *Length of peduncle.*—6.5-9.5 cm.
- *Peduncle diameter.*—0.15 cm.
- *Texture.*—Bifid T-shaped hairs.

Inflorescence:
- *Type.*—Compositae type, solitary inflorescences (decorative-type) borne terminally above foliage, ray florets arranged acropetally on a capitulum.
- *Natural season flowering.*—About mid September.
- *Quantity of inflorescences per plant.*—About 30 with numerous buds.
- *Lastingness of individual blooms on the plant.*—3-4 weeks.
- *Fragrance.*—Slightly spicy.

BUD: (Just when opening/showing color)
- *Color.*—Between RHS 1A and RHS 1B.
- *Length.*—0.7-1.0 cm.
- *Width.*—1.0-1.4 cm.
- *Shape.*—Oblate.

Immature inflorescence:
- *Diameter.*—4.0 cm.
- *Color of ray florets, upper surface.*—RHS 6B.
- *Lower surface.*—RHS 5C.

Mature inflorescence:
- *Diameter.*—5.5-6.3 cm.
- *Depth.*—1.3-1.4 cm.
- *Total diameter of 'disc'.*—2.5-2.9 cm.
- *Receptacle height.*—0.35-0.4 cm.
- *Receptacle diameter.*—0.5-0.6 cm.

Ray florets:
- *Average quantity of florets.*—About 20-30 fully developed in 2 whorls.
- *Color of florets, upper surface.*—RHS 6B.
- *Lower surface.*—RHS 5C.
- *Length.*—2.5-2.7 cm.
- *Width.*—0.6 cm.
- *Shape.*—Elliptical.
- *Apex shape.*—Rounded to obtuse.
- *Margin.*—Entire.
- *Texture, upper surface.*—Papillose.
- *Lower surface.*—Papillose.

Disc florets:
- *Average quantity of florets.*—About 150-175.
- *Color of florets.*—RHS 5B with RHS 1C basally.
- *Length.*—0.8-0.9 cm.
- *Width.*—0.2 cm.
- *Shape.*—Tubular, elongated.
- *Apex shape.*—Acute, 5 pointed and deeply split.

Phyllaries:
- *Quantity.*—About 25-27.
- *Color, upper surface.*—RHS 146B.
- *Lower surface.*—RHS 146B.
- *Length.*—0.6-0.7 cm.
- *Width.*—0.1-0.2 cm.
- *Shape.*—Ovate.
- *Apex shape.*—Acute.
- *Based.*—Fused.
- *Margins.*—Entire.
- *Texture, upper surface.*—Bifid T-shaped hairs.
- *Lower surface.*—Bifid T-shaped hairs.

Reproductive organs:
- *Pistil.*—1.
- *Length.*—0.5 cm.
- *Style color.*—RHS 1B but somewhat more translucent.
- *Style length.*—0.4 cm.
- *Stigma color.*—RHS 5B.
- *Stigma shape.*—Bi-parted.
- *Ovary color.*—RHS 155C.
- *Stamens.*—1.

*Color of filaments.*—RHS 1C.
*Length filaments.*—0.25 cm.
*Anther color.*—RHS 161D.
*Anther length.*—0.1 cm.
*Anther shape.*—Oblong.
*Color of pollen.*—RHS 7C.
*Pollen amount.*—Scarce.
*Fertility/seed set.*—Has not been observed on this hybrid.

Disease/pest resistance: Disease/pest resistance as not been observed on this hybrid.

What is claimed is:

1. A new and distinct variety of *Chrysanthemum* plant named 'Synberna Yel' substantially as illustrated and described herein.

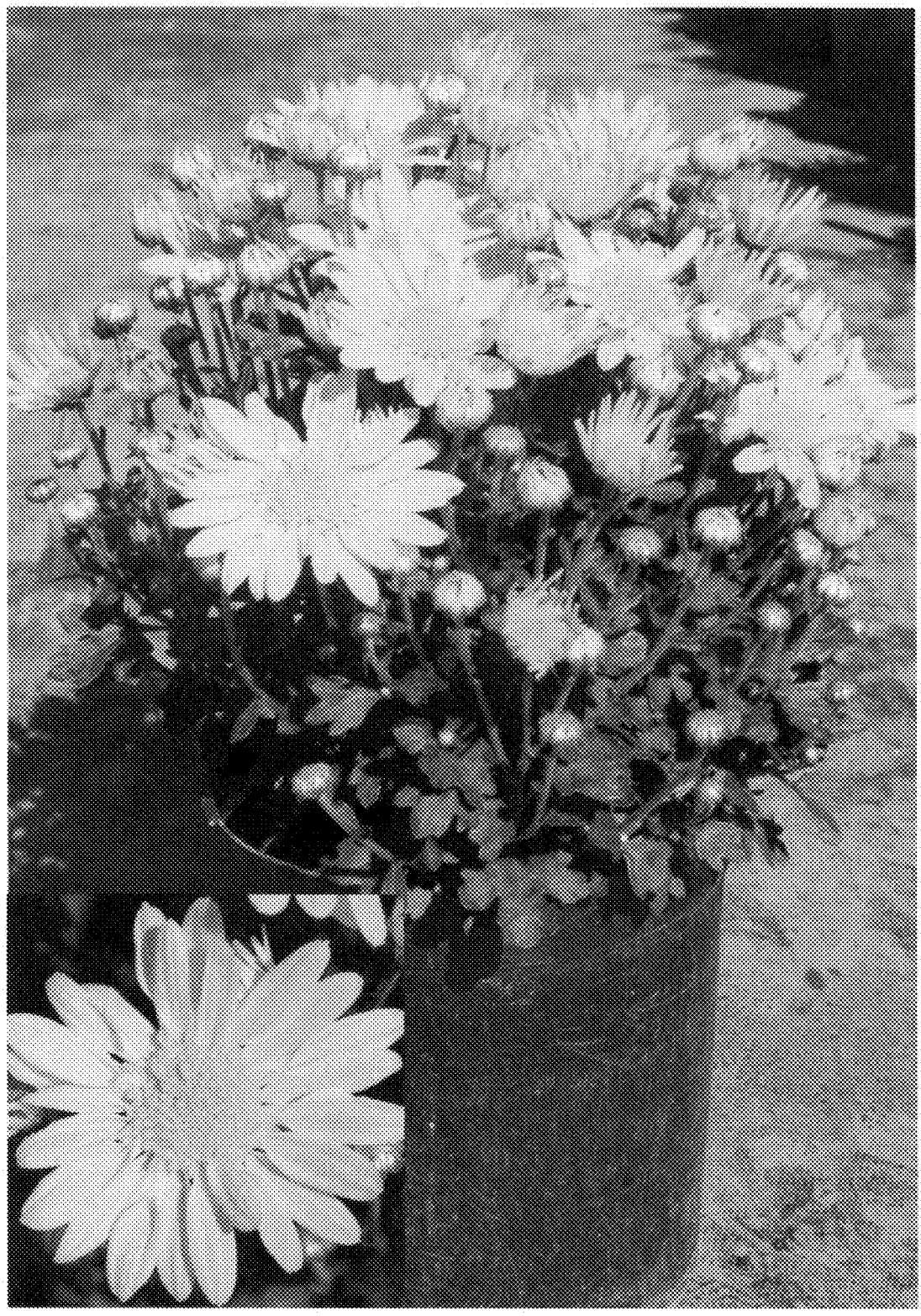

* * * * *